United States Patent [19]

Fitzgerald et al.

[11] 4,299,119
[45] Nov. 10, 1981

[54] INCREMENTAL ROTARY VISCOMETER

[75] Inventors: J. Vincent Fitzgerald, Metuchen; Frank J. Matusik, Piscataway; Donald W. Nelson, Voorhees, all of N.J.

[73] Assignee: National Metal and Refining Company, Ltd., Edison, N.J.

[21] Appl. No.: 129,984

[22] Filed: Mar. 13, 1980

[51] Int. Cl.³ .............................................. G01N 11/14
[52] U.S. Cl. ............................................................ 73/59
[58] Field of Search ............................................ 73/59

[56] References Cited

U.S. PATENT DOCUMENTS

| | | | |
|---|---|---|---|
| 2,365,339 | 12/1944 | Green | 73/59 |
| 2,657,572 | 11/1953 | Fann | 73/59 |
| 2,736,195 | 2/1956 | Christianson | 73/59 X |
| 3,079,788 | 3/1963 | Trotin | 73/59 |
| 3,875,791 | 4/1975 | Fitzgerald et al. | 73/59 |
| 3,901,070 | 8/1975 | Duffy | 73/59 |

FOREIGN PATENT DOCUMENTS 1251560 10/1971 United Kingdom ................... 73/59

Primary Examiner—Charles A. Ruehl
Assistant Examiner—Joseph W. Roskos
Attorney, Agent, or Firm—Arthur L. Lessler

[57] ABSTRACT

A rotary viscometer of the type which measures the viscous torque to which a rotating spindle is subjected, by measuring the current drawn by the electric motor driving the spindle. True viscosity, i.e. the slope of the torque-spindle rotation speed curve, is approximated by varying the spindle speed stepwise in sets of speed measurements having a fixed speed difference, and obtaining the difference between the corresponding torque values for each set. By repeating this process throughout the desired speed range, an approximate derivative of the torque-speed curve is obtained, corresponding to an approximation of the true viscosity of the fluid being characterized.

25 Claims, 5 Drawing Figures

| RANGE | LOW | MEDIUM | HIGH |
|---|---|---|---|
| SPEED (rpm) | 0.5-5 (0.1-4.6) | 5-50 (1-46) | 50-500 (10-460) |
| NO. OF SAMPLES PER Δ SPEED STEP | 1 | 2 | 4 |
| NO. OF SAMPLES PER STAIRCASE STEP | 2 | 4 | 8 |
| Δ SPEED | 0.4 rpm | 4 rpm | 40 rpm |
| STAIRCASE SPEED INCREMENT | 0.018 rpm | 0.18 rpm | 1.8 rpm |
| STAIRCASE SPEED STEP DURATION (WITH DOUBLE FLAG) | 1 rev. | 4 rev. | 8 rev |

FIG. 4

INCREMENTAL ROTARY VISCOMETER

BACKGROUND OF THE INVENTION

This invention relates to a rotational viscometer apparatus and a process utilizing the same for measuring the viscosity of a fluid medium; and more particularly to an apparatus and process capable of approximating the true viscosity of non-Newtonian fluids.

Various techniques are known in the art for the repetitive or continuous measurement of the viscosity of Newtonian fluids, and a number of such arrangements are described in the introductory portion of U.S. Pat. No. 3,875,791, the invention of which relates to a rotary viscometer capable of providing a true indication of the viscosity of Newtonian fluids, and of characterizing a fluid as to its Newtonian or non-Newtonian character.

The rotary viscometer of U.S. Pat. No. 3,875,791, rotates a fluid shearing spindle in a cup containing the fluid to be characterized, at a rotation speed which can be scanned across a desired range; and provides a plot of fluid shearing torque to which the spindle is subjected, as a function of spindle rotation speed. If the torque increases linearly with speed, the fluid is Newtonian, with a viscosity equal to the torque/speed ratio. If the torque variation with speed is non-linear, the fluid is non-Newtonian.

While the rotary viscometer arrangement of U.S. Pat. No. 3,875,791 is thus quite accurate and useful in connection with Newtonian fluids, it is incapable of directly providing true viscosity information for non-Newtonian fluids. For such non-Newtonian fluids, an effective differentiation of the torque-speed curve is required, since the true viscosity of the non-Newtonian fluid at any given spindle rotation speed is proportional to the slope of the torque-speed curve at such speed.

Accordingly, an object of the present invention is to provide an improved rotary viscometer which is capable of not only generating torque vs. spindle rotation speed curves, but also of generating information respecting the approximate true viscosity of non-Newtonian fluids.

SUMMARY

As herein described, there is provided a process for determining the viscosity of or viscous loss in a fluid, comprising the steps of: (a) providing a rotatable fluid shearing spindle adapted for immersion in said fluid; (b) rotating said spindle at a first speed determined by a speed sweep signal, said first speed lying within a predetermined speed range having upper and lower speed limits; (c) measuring the torque exerted by said fluid on said spindle at said first speed; (d) subsequently varying said first speed by a given speed difference, to a second speed within said range, said first and second speeds comprising a set of speed values; (e) measuring the torque exerted by said fluid on said spindle at said second speed; (f) providing a viscosity or viscous loss indicating signal for said set corresponding to the difference between said first and second speed torque values; and (g) thereafter causing said spindle speed to successively assume other sets of first and second speed values throughout said range, in accordance with said speed sweep signal, and repeating steps (c) through (f) for each of said successive other sets of speed values.

Also herein described is apparatus for determining the viscosity of or viscous loss in a fluid, comprising: (a) a rotatable fluid shearing spindle adapted for immersion in said fluid; (b) a motor and associated means for rotating said spindle at a first speed determined by a speed sweep signal, said first speed lying within a predetermined speed range having upper and lower speed limits, and for providing an output signal indicative of the torque applied to said spindle by said fluid; (c) a first sample-and-hold circuit for storing the value of said output signal indicative of the torque exerted by said fluid on said spindle at said first speed; (d) means for subsequently varying said first speed by a given speed difference, to a second speed within said range, said first and second speeds comprising a set of speed values; (e) a second sample-and-hold circuit for storing the value of said output signal indicative of the torque exerted by said fluid on said spindle at said second speed; (f) a difference circuit means for providing a viscosity or viscous loss indicating signal corresponding to the difference between said first and second speed torque values; and (g) means for varying said sweep speed signal to thereafter cause said first and second spindle speeds to successively assume other sets of speed values throughout said range.

IN THE DRAWING

FIG. 1b is an enlarged portion of part of the graph shown in FIG. 1a;

FIG. 4 is a table of parameters respecting the operation of the circuit of FIG. 2 in various speed ranges.

DETAILED DESCRIPTION

Figure 1A:
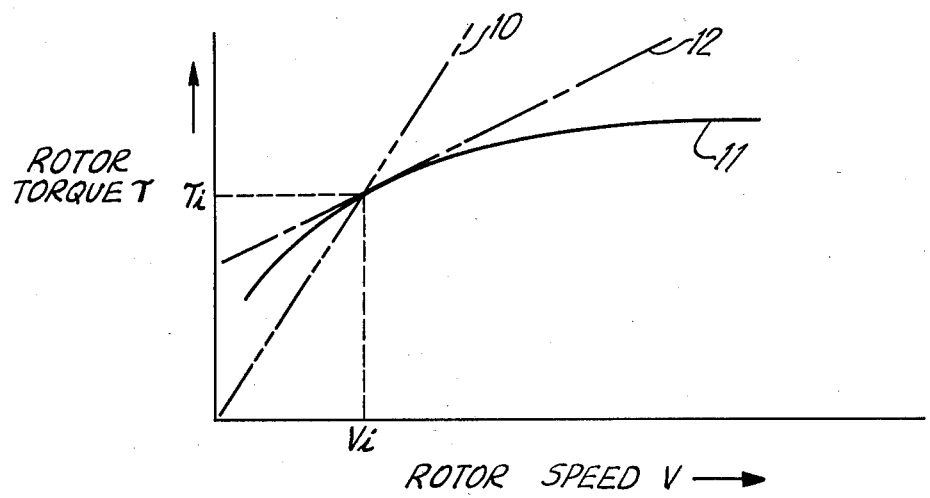
FIG. 1a is a graph useful in explaining the operation of the present invention.
Figure 2:
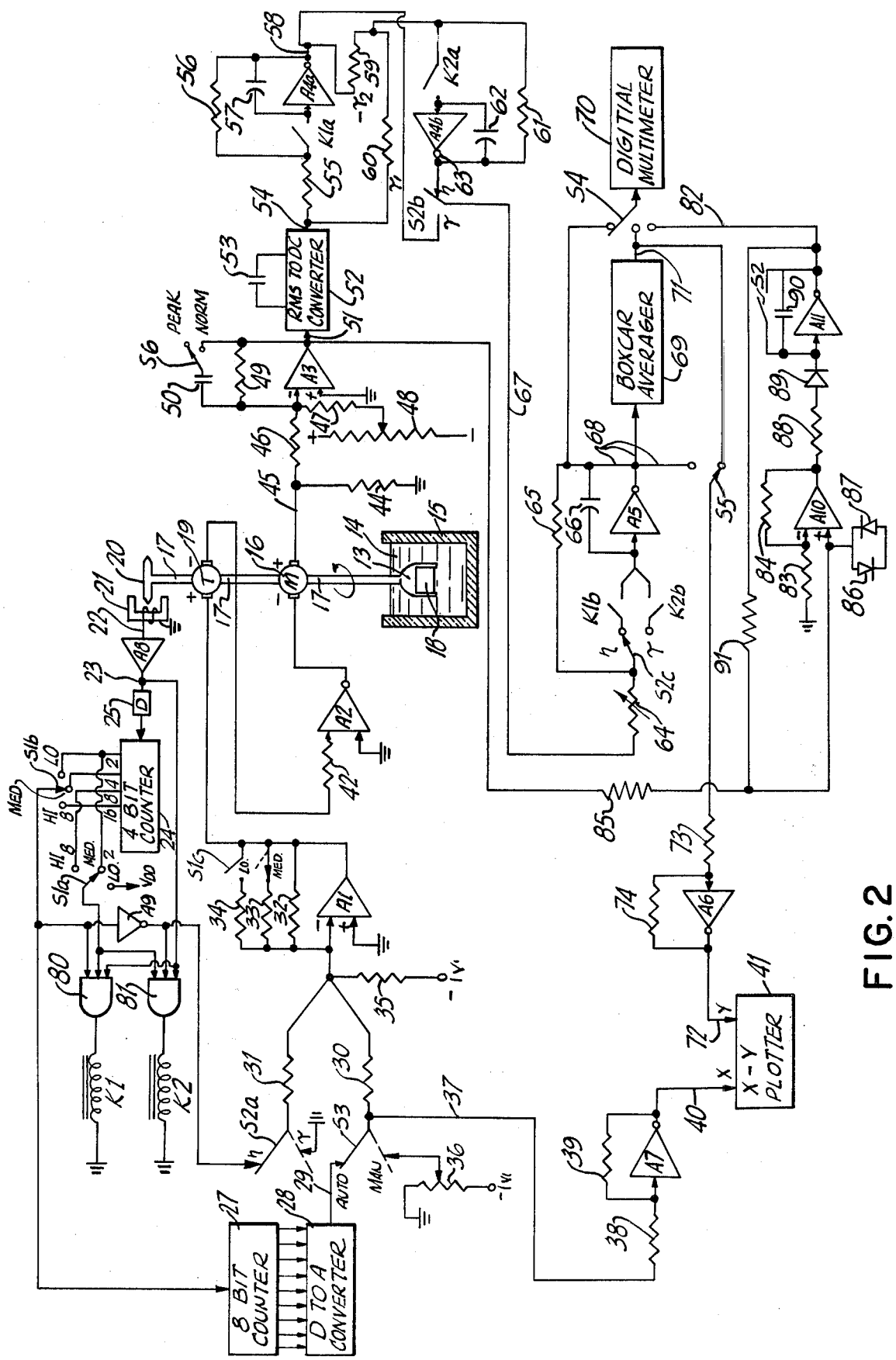
FIG. 2 is a functional block diagram of an incremental rotary viscometer according to a preferred embodiment of the invention.

Utilizing the known type of rotary viscometer described in U.S. Pat. No. 3,875,791, it is possible to obtain a plot of spindle or rotor torque $\tau$ as a function of rotor rotational speed v, as shown in FIG. 1a. For a Newtonian fluid, this plot would be a straight line passing through the origin (after calibration to eliminate torque forces due to motor friction and ohmic, hysteresis and other losses), e.g. the line 10. Cf. FIG. 2 of U.S. Pat. No. 3,875,791.

In the case of a non-Newtonian fluid, the torque vs speed characteristic would be a curve such as the curve 11.

In mathematical terms, the true viscosity of any fluid is defined by the expression $$\eta = \frac{\partial \tau}{\partial D} = C_o \frac{\partial \tau}{\partial v} \tag{1}$$

where
 $\eta$ = true viscosity
 $\tau$ = spindle torque generated by fluid
 D = fluid shear rate
 v = rotational speed of spindle
 $C_o$ = a constant The fluid shear rate D is the velocity gradient between infinite parallel plates having the fluid disposed therebetween and moving at relative velocity V with respect to each other, i.e. D = grad V. This gradient is closely approximated when a fluid is sheared along a narrow annulus thereof by rotating a relatively large radius spindle in close proximity to the inner wall of a cup holding the fluid, i.e. $D \approx v/w$, where w is the width of the fluid annulus being sheared. Thus, for a given spindle-cup system D is proportional to v.

For a Newtonian fluid, having the torque vs speed curve 10, where torque is directly proportional to rotor speed, this equation simplifies to $$\eta = C_1 \frac{\tau}{v} \quad (2)$$

where $C_1$ = a constant and for this Newtonian fluid the viscosity at rotor speed $v_i$ is obtained by dividing the corresponding torque $\tau_i$ by said speed $v_i$.

This division operation is in fact performed by the circuitry shown in U.S. Pat. No. 3,875,791, which circuitry is capable of providing plots of both viscosity (for Newtonian fluids only) and torque as a function of rotor speed.

If, however, the fluid is non-Newtonian and has a characteristic such as that indicated by the curve 11, the true viscosity of the fluid at point $\tau_i$, $v_i$, corresponds to the slope of the torque-speed curve at that point, i.e. the slope of the line 12, which is obviously quite different from the slope of the line 10 through the origin.

The present invention improves upon the arrangement of U.S. Pat. No. 3,875,791 insofar as the measurement of viscosity of non-Newtonian fluids is concerned, by approximately differentiating the torque vs speed curve 11, to provide an output signal approximating the slope of the curve at each rotor speed within a desired range.

Figure 1B:
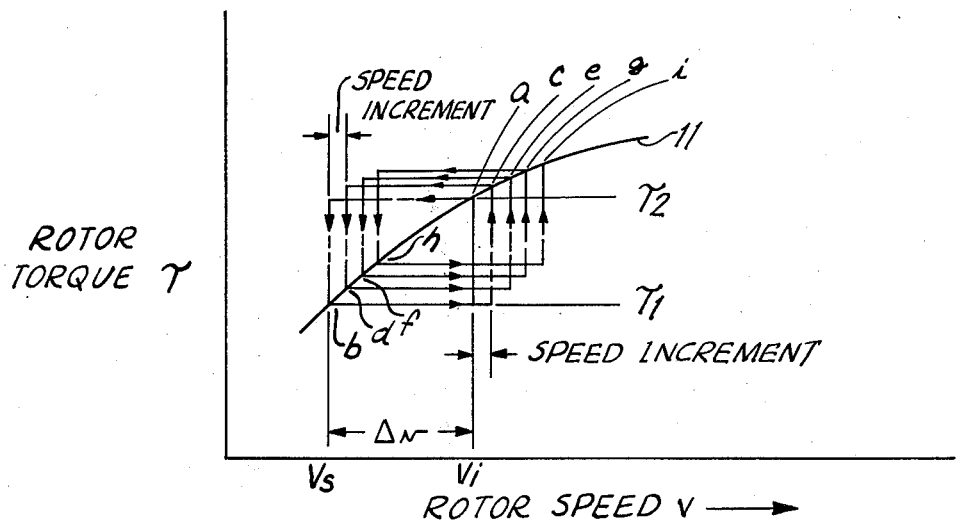

The manner in which this approximate differentiation is carried out will be most clearly understood by reference to FIG. 1b, which shows an expanded portion of the torque vs speed curve 11.

By measuring the torque at various discrete points of the curve 11, said points being separated by a speed difference $\Delta v$, the true viscosity can be approximated by approximating equation (1) as follows:

$$\eta \approx \frac{\Delta \tau}{\Delta v} = \frac{\zeta(v + \Delta v) - \zeta(v)}{\Delta v} \quad (3)$$

To provide as accurate as possible an approximation of the slope of the torque-speed curve, it would be desirable to employ very small values of speed difference, determine the corresponding small values of torque difference, and divide the latter by the former value. However, the use of very small speed differences, while within the scope of the present invention, results in the necessity for determining small differences between relatively large numbers, with resultant high noise levels and inaccuracies. Therefore a somewhat different incremental approach is employed in the apparatus and process of the preferred embodiment of the invention.

In order to provide a reasonable size of the speed difference for slope measurements, while also providing a large number of measurements for averaging purposes to provide improved accuracy and reliability, the slope of the curve 11 is determined in a stepped series of nested speed difference sets of measurements. For example, the rotor speed v may be brought to an initial value $v_i$ corresponding to point a of the curve 11. The corresponding torque value $\tau_2$ is then determined by the apparatus and stored.

Immediately thereafter the rotor speed is reduced by a predetermined speed difference $\Delta v$, to a second speed $v_s$, and the corresponding torque value $\tau_1$ is also stored. The difference between this set of torque measurements, i.e. $\tau_2$ minus $\tau_1$, is proportional to an approximate value of the slope of the curve 11 in the region between $v_s$ and $v_i$. Division by the speed difference $\Delta v$ is not necessary if the same speed difference is maintained for all subsequent sets of torque difference measurements, as is done according to the preferred embodiment of the invention.

After the second measurement of the set has been taken as indicated above (at point b of the curve 11), the rotor speed is increased to $v_i$ plus a predetermined speed increment which is substantially less than the speed difference $\Delta v$, to move the rotor speed to a value corresponding to point c of the curve 11. The corresponding torque value is stored, and the rotor speed is again decreased by the speed difference $\Delta v$, to a value corresponding to point d of the curve 11, the corresponding torque value being stored. The difference between the torque values corresponding to points c and d thus provides another measurement of the slope of the curve 11 at a point slightly displaced from the point at which the first slope measurement was made.

Thereafter the process of rotor speed increase and decrease is repeated, with successive sets of torque measurements being taken and the differences between the corresponding torque values being computed. For the rotor speed changes shown in FIG. 1b, sets of torque difference (corresponding to approximate true viscosity) measurements are taken for the rotor speed sets a/b, c/d, e/f and g/h. Thus a number of true viscosity computations are carried out corresponding to closely spaced points of the curve 11. Filtering and averaging of the resulting information provides a good approximation of the true viscosity of the fluid being characterized.

Suitable apparatus for carrying out the process explained with reference to FIG. 1b is shown in FIG. 2, wherein a fluid shearing spindle 13 is immersed in a fluid 14 to be characterized, said fluid being disposed within a container 15 having inner cylindrical walls, with the major surface portions of the spindle 13 preferably also being cylindrical and coaxial with the inner cylindrical walls 15.

The spindle 13 is supported and rotated by a motor 16 via a shaft 17. In order to minimize thrust on the bearings of the motor 16, it is preferable that the spindle 13 be completely immersed in and at least partially supported by the fluid 14, with fluid being kept out of the inner portion of the spindle 13 by a pocket of entrapped air 18. Alternatively, other means of supporting the spindle, such as use of light weight metals or plastics for the spindle material to increase buoyancy, an axial bearing touching the bottom of the fluid container, or an air cushion bearing may be employed.

The speed of rotation of the shaft 17 is measured by a tachometer generator 19, and a rotary flag element 20 (shown as a magnetic wheel having two notches (not visible) spaced 180 degrees apart) is also mounted on the shaft 17, for cooperation with the magnetic pickup 21 to provide an output pulse to preamplifier A8 on line 22 for each half revolution of the shaft 17. In several models constructed, the element 20 was a photoelectric interrupter, which functioned satisfactorily without the need for a preamplifier.

Corresponding output "clock" pulses from the preamplifier A8 on line 23 are counted (after a delay introduced by the delay circuit 25) by the four bit counter 24, which provides outputs from the four stages thereof having periods corresponding to receipt of 2, 4, 8 and 16 pulses on line 23 respectively. The circuit 25 introduces a delay on the order of 2 milliseconds, so that speed changes are not initiated until after the corresponding relays K1 and K2 have been de-energized, thus insuring that transient effects associated with motor speed changes and fluid inertia do not adversely affect the system performance.

The apparatus of FIG. 2 has three ranges of rotational speed of the shaft 17, viz. (LO) 0.5 to 5 rpm, (MED) 5 to 50 rpm, and (HI) 50 to 500 rpm. Obviously, other ranges (decade or otherwise) may alternatively be employed.

The relay coil of a relay K1 is connected to the output of the counter 24 and preamplifier A8, through range selector switches S1a and S1b and AND gate 80, to selectively sample the torque to which the spindle 13 is subjected by the fluid 14 (by monitoring the armature current through the motor 16), during time intervals (corresponding to about 5 degrees of shaft rotation) when the spindle speed is at the higher of the two values of each set.

Similarly, the relay coil of a relay K2 is connected to the output of the counter 24 and preamplifier A8, through range selector switches S1a and S1b, inverting amplifier A9 and AND gate 81, to selectively sample the torque to which the spindle 13 is subjected by the fluid 14 (by monitoring the armature current through the motor 16), during time intervals (corresponding to about 5 degrees of shaft rotation) when the spindle speed is at the lower of the two values of each set.

Figure 3:
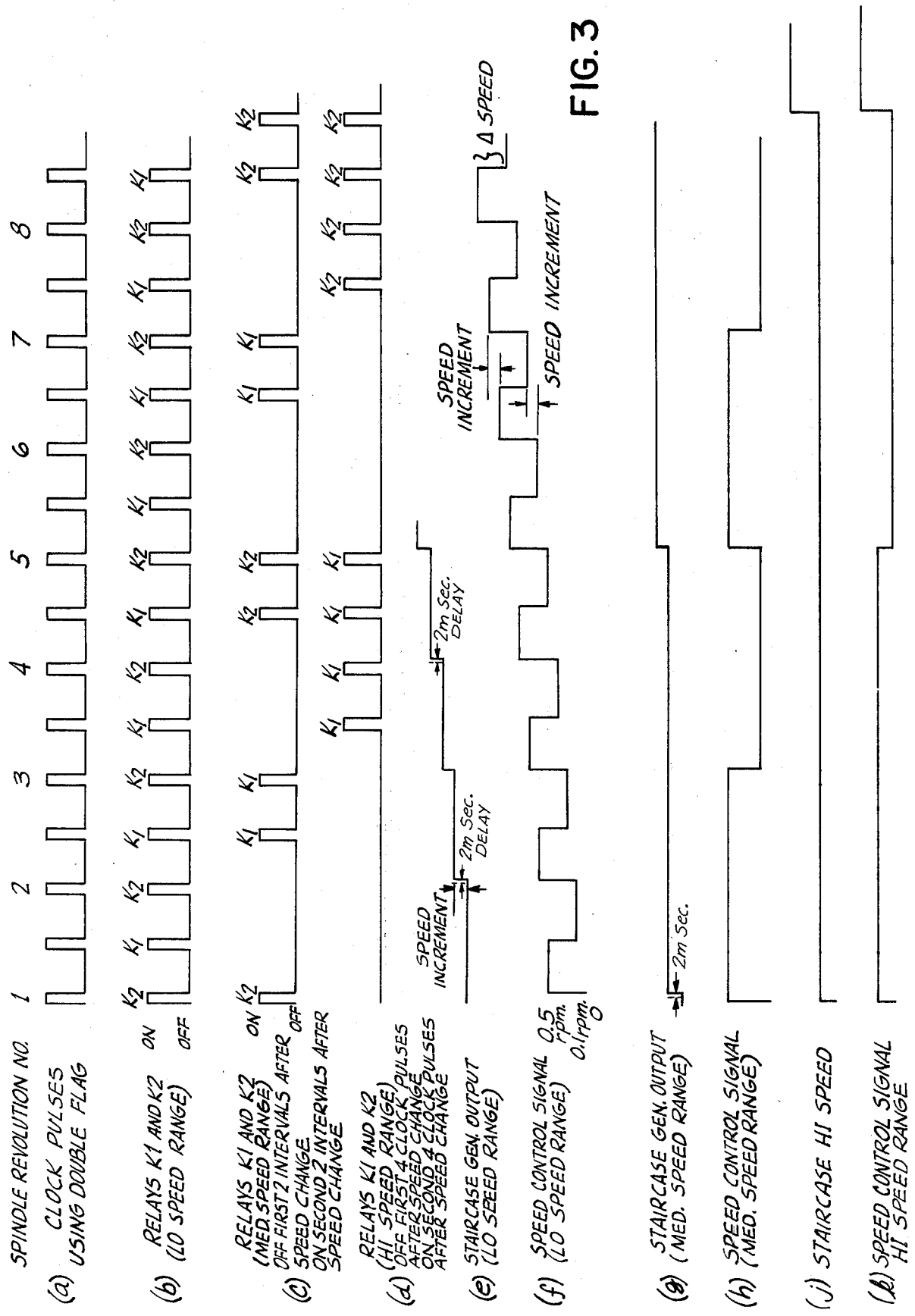
FIG. 3 is a timing diagram showing the interrelationship between various waveforms present in the circuit of FIG. 2.

The pulses on line 23 are shown as waveform (a) of FIG. 3, and have a duration corresponding to about 5 degrees of rotation of the spindle 13 and shaft 17. Waveform (b) shows the energization of relays K1 and K2 when section a of the range selector switch S1 is in the low and medium speed positions; from which it will be noted that each relay has a sampling time equal to the duration of the corresponding clock pulse. Waveform (c) of FIG. 3 shows the energization of relays K1 and K2 when switch section S1a is in the high speed position.

The output of counter 24 is coupled to (i) an 8 bit counter 27 and (ii) a section S2a of function selector switch S2 via section S1b of the range selector switch S1.

The switch S2 selects either (A) a torque mode, in which viscous torque is measured, or (B) a viscosity mode, in which approximate true viscosity is measured. In both the torque and viscosity modes, the measurement can be made either at a single selected speed (in the manual position of the mode selector switch S3) or over a range of speeds (in the automatic position of the switch S3).

In the viscosity indicating position of the switch S2, the approximate differentiation operation previously described with respect to FIG. 1b is carried out, to approximate the true viscosity of non-Newtonian fluids and give a more or less exact measurement of viscosity of Newtonian fluids.

Since the operation of the apparatus in the manual mode (i.e. without automatic speed scanning), and operation in the torque measuring function position of switch S2 will be obvious after operation of the viscosity indicating function is explained, no separate explanation of the other functions and modes is considered necessary.

Each of the amplifiers A1 through A11 is an inverting operational amplifier, with the amplifiers A1 to A3 and A10 utilizing differential input terminals. The other amplifiers also have differential input terminals, wherein the positive input, when not shown, is returned to ground. All of said amplifiers are capable of DC operation and have upper frequency limits sufficient to handle the alternating current components of the signals processed thereby.

Amplifier A1 is connected to operate as a summing amplifier; A2 serves as a power amplifier and a driver for the motor 16; A3 is a normalizing amplifier and filter; A4a and A4b are sample and hold circuits; A5 is a sample and hold stage; and A6 and A7 are plotter drive amplifiers.

The output of the counter 24 is coupled to an 8 bit counter 27, with the output of the counter 27 being coupled to a digital to analog converter 28.

The counter 27 counts from zero up to 255, then returns to zero and resumes counting again. In the low speed position of the switch section S1b, the counter 27 counts by 1 for each revolution of the shaft 17, and completes one full count sequence (including one high speed interval and one low speed interval) of 256 counts for 256 revolutions of said shaft.

The output of the digital to analog converter 28 on line 29 is therefore a staircase waveform, with the duration of each step corresponding to the duration of the corresponding count of the counter 27. The staircase waveform on line 29 has 255 steps for each count sequence of the counter 27, generating a repetitive staircase waveform each time the counter 27 resets. Waveform (e) of FIG. 3 shows a portion of the signal on line 29, when switch S1b is in its low speed position, while waveform (g) shows the signal on said line when S1b is in its medium speed position.

The counter 27 may be connected to count up, down, or alternately up and down (with, if desired, a predetermined time delay between successive counts), in successive count sequences of 255 steps each. Obviously, other numbers of steps in each count sequence could also be employed if so desired.

Thus the staircase signal on line 29 is applied as one input to summing amplifier A1 via switch S3 and summing resistor 30, while a square wave synchronized therewith is applied to another input of summing amplifier A1 via switch section S2a and summing resistor 31. The effective input signal to summing amplifier A1 (and the voltage analog of the output signal thereof) has a waveform as shown in (f) of FIG. 3 when switch S1b is in its low speed position. This composite waveform represents the speed control signal generated by summing amplifier A1.

Switching of speed ranges is effected by varying the gain of amplifier A1, with feedback resistor 32 being operative in the high range, feedback resistor 32 and 33 being operative in the medium range, and feedback resistors 32 and 34 being operative in the low range. Selective engagement of resistors 33 and 34 is accomplished by means of section S1c of range switch S1.

In the medium speed position of switch S1, the waveform applied to amplifier A1 through summing resistor 31 is shown as waveform (h) in FIG. 3.

The bias resistor 35 sets the input of amplifier A1 at the value required to provide the desired minimum speed for each range.

Summing amplifier A1 and its associated circuitry, together with motor 19, is designed to provide the previously described speed ranges, i.e. as shown in FIG. 4. Since the step waveform on line 29 contains 255 steps for traversing each speed range, the corresponding size of each speed increment as 1/255th of the range. For the low range, the speed increment size is therefore $(5-0.5)/255=4.5/255=0.018$ rpm speed increment. In this range the speed difference between the higher and lower speeds of each set of readings is preferably on the order of 0.4 rpm.

Similarly, in the medium speed range the speed increment between successive sets of readings is 0.18 rpm while the speed difference is preferably on the order of 4 rpm; and in the high speed range the speed increment is 1.8 rpm while the speed difference is preferably on the order of 40 rpm.

The manner in which speed is varied and torque samples are taken will be best understood by reference to waveforms (b) and (f) of FIG. 3.

Each step of the staircase waveform shown at (e) of FIG. 3 comprises one measurement cycle. At the end of the first portion of this cycle relay K1 is energized and the spindle 13 is rotated at a speed of 0.5 rpm, for half a revolution. The time duration of this portion is therefore 0.5 revolution/0.5 rpm = 1 minute.

After this first half revolution, relay K1 is deenergized, with relay K2 being energized at the end of the second half revolution, and the speed of rotation of the spindle 13 is reduced by the 0.4 rpm speed difference, i.e. to 0.1 rpm. During this second portion of the first cycle, the spindle 13 rotates for a time duration equal to 0.5 revolution/0.1 rpm = 5 minutes.

As a result of energization of relays K1 and K2 as stated above, corresponding torque samples are taken during the first and second portions of the measurement cycle. These torque readings are subsequently subtracted from each other to provide a torque difference signal indicative of true viscosity.

At the end of the first measurement cycle, the output of staircase generator or digital to analog converter 28 advances by an amount corresponding to the desired 0.018 rpm speed increment, to an amplitude corresponding to a spindle speed of 5.018 rpm. This speed is maintained during the first portion of the second measurement cycle, at the end of which relay K1 is energized. At the end of the first portion of the second measurement cycle, the speed of spindle 13 is reduced by the 0.4 rpm speed difference, i.e. to 0.118 rpm, and relay K2 is thereafter energized at the end of the second portion of the second measurement cycle.

This process of providing higher and lower speeds for the first and second portions of each step, with a fixed speed difference between, and speed increments between the first portion of each step and the first portion of the preceding step which are equal to the speed increments between the second portion of each step and the second portion of the preceding step, the speed increments being substantially less than the speed difference between the first and second portions of each step, is repeated until the entire speed range has been traversed.

For each step of the staircase generated by the converter 28, each of the relays K1 and K2 is energized to provide one sample of the torque reading corresponding to the higher speed and one sample of the torque reading corresponding to the lower speed for the corresponding step, in the low speed range.

In the medium speed range, as best seen in waveform (h) of FIG. 3, each of the relays K1 and K2 is energized to take two torque reading samples per step of the staircase generator 28, with the circuit operation in all other respects remaining essentially the same.

In the high speed range the relays K1 and K2 are energized by the third output line (count-by-eight) of the counter 24, so that each of the relays takes four samples during each speed interval comprising two full revolutions of the shaft 17, as best seen in waveform (d) of FIG. 3. In this high range, the switch section S1b is coupled to the last stage of the counter 24 (count-by-sixteen), so that each step of the staircase waveform appearing on line 29 has a duration corresponding to 8 revolutions of the shaft 17.

More specifically, the third output line of the counter 24 defines the basic speed timing period. Because of the AND gate system comprising gates 80 and 81, the relay K1 is energized on the last four clock pulses of the basic eight count period. Relay K2 is energized on the last four clock pulses of the next succeeding count of eight. The first four counts of each period (on the high speed range) are not utilized for sampling, in order to allow for the speed switching transient to settle. This arrangement is evident by reference to the timing diagram of FIG. 2, and is applicable to any speed change.

On the medium speed range, the basic speed timing period is four counts (two of which are sampling pulses), defined by the second output line of the counter 24.

On the low speed range, the basic speed timing period is one count, one sample is taken during each speed interval, and the settling time allowed is the difference between the 180 degree flag time and the 5 degree flag width.

The reason why the timing is such that two and four samples per step are taken in the medium and high speed ranges respectively is primarily to provide optimum performance in view of fluid turbulence and other noise-producing factors.

With the mode switch S3 in the manual position, potentiometer 36 is adjusted to rotate the shaft 17 at any desired initial speed, and approximate true viscosity at said speed is provided by varying the speed between the initially set value and a value which is 0.4, 4 or 40 rpm less (depending on the setting of the range switch S1), with circuit operation being substantially the same as previously described, except that instead of a staircase waveform being coupled to the input side of the summing resistor 30, a DC level is coupled thereto.

The input signal to summing resistor 30 is also coupled on line 37 to a fixed gain plotter drive amplifier A7, the gain of which is set by input and feedback resistors 38 and 39 respectively. The output of amplifier A7 on line 40 is coupled to the horizontal or X coordinate input of the plotter 41 and comprises a voltage the level of which corresponds to the rotational speed of the shaft 17.

The output of amplifier A1 is coupled in series with the tachometer generator 19, through an input resistor 42, to the inverting input terminal of motor drive amplifier A2, the gain of said amplifier being set by the feedback provided by the tachometer generator 19, thereby providing a constant speed servo system suitable for variable loads.

The output of amplifier A2 is coupled to the series combination of the armature winding of drive motor 16 and current sensing resistor 44, the value of which is relatively small compared to the effective impedance of motor 16.

The aforementioned servomechanism arrangement operates to drive motor 16 so that the voltage developed across the terminals of tachometer generator 19 is equal to the output voltage of amplifier A1 corresponding to the desired speed. Thus motor 16 is caused to rotate at a speed corresponding to the sum of the inputs through summing resistors 30 and 31, adjusted by the closed loop gain of amplifier A1.

The motor 16 is preferably of the permanent magnet DC type, with an armature wound on a hollow non-magnetic core. A suitable motor for this purpose is a two-pole, permanent magnet DC ironless motor manufactured by Portescap, a Swiss company having offices in New York City, New York. Specific characteristics of this motor are described in the portion of U.S. Pat. No. 3,875,791 running from column 6, line 54 to column 7, line 12. Alternatively, other types of motors having low inertia and linear current-torque characteristics may be employed.

Thus the motor drive current, which passes through current sensing resistor 44, develops a voltage at point 45 which is directly proportional to motor torque (plus residual motor current). The torque signal at point 45 is coupled to the inverting input terminal of normalizing amplifier A3 through input resistor 46, potentiometer 48 and bias resitor 47 serving for adjustment to balance out the residual motor armature current due to friction and other losses.

The gain of normalizing amplifier A3 is established by feedback resistor 49 in conjunction with input resistor 46. Capacitor 50 serves to provide high frequency filtering of transients due to the sudden motor speed changes necessitated by the operation of the system.

The output of normalizing amplifier A3 on line 51 is coupled to the input terminal of an rms (root mean square) to DC converter 52, with additional filtering for the signal being processed being provided by the capacitor 53.

A suitable rms to DC converter is that marketed by Analog Devices, Inc., Route 1 Industrial Center, Norwood, Massachusetts 02062, as Model No. 536, said device being described in a publication of said company entitled "Data Acquisition Products" 1978, pages 229 to 234.

The output of rms to DC converter 52 on line 54 has a waveform generally resembling waveform (b) of FIG. 3 in the low and medium speed ranges, and waveform (c) thereof in the high speed range, with rounded edges at the transitions. In this waveform, the amplitude during times when relay K1 is energized corresponds to the higher speed torque value of each set of differential readings, and the amplitude during the time that relay K2 is energized corresponds to the lower torque value of the set. Therefore, by taking successive torque samples when relays K1 and K2 are energized, and subtracting each K2 sample from the preceding K1 sample, a difference signal approximately corresponding to true viscosity is provided.

Sampling of the torque indicating signal on line 54 during the time relay K1 is energized is accomplished by the sample-and-hold circuit comprising amplifier A4a, input resistor 55, feedback resistor 56, holding capacitor 57, and relay contacts K1a of relay K1. These elements form a conventional inverting sample-and-hold circuit, the operation of which need not therefore be described in any detail.

The output of amplifier A4a on line 58 is therefore a slowly varying, essentially DC signal, with transitions occurring at the times relay K1 is energized. The higher speed torque indicating signal sample on line 58 is coupled to (i) the torque selection terminal of section S2b of function switch S2 and (ii) a summing amplifier sample-and-hold circuit comprising input resistors 59 and 60, feedback resistor 61, switch contacts K2a of relay K2, amplifier A4b, and holding capacitor 62.

The higher speed torque indicating sample on line 58 is coupled to the input side of summing resistor 59, while the torque indicating signal on line 54 is coupled to the input side of summing resistor 60. That is, the input to summing resistor 59 at all times corresponds to the most recently taken sample of the fluid shearing torque corresponding to the higher speed of each set of readings taken during one speed step of the staircase waveform on line 29; while the input to summing resistor 60 corresponds to the torque then being experienced by the spindle 13.

When relay contacts K2a are closed (i.e. when relay K2 is energized), the input signal to summing resistor 60 corresponds at that time to the low speed torque sample to be taken during the corresponding step of the staircase waveform on line 29. At this time, due to the inverting operation of the amplifier A4a, the input to summing resistor 59 is the negative of the higher speed torque sample. Thus the sum of the signals applied to input resistors 59 and 60 is the negative of the difference between the higher speed and lower speed torque samples taken during the corresponding step (or part thereof), on all ranges.

This difference signal is sampled by amplifier A4b and held by capacitor 62, so that the output of amplifier A4b on line 63 is a signal proportional to the difference between the torque readings corresponding to the higher and lower speeds (with the aforementioned 0.4, 4 or 40 rpm speed difference therebetween) of successive energizations of the relays K1 and K2.

The output signal of amplifier A4b on line 63 is thus essentially a DC level which changes relatively slowly, and undergoes a more or less abrupt transition when relay Ka is energized.

The output of amplifier A5 on line 68 is a varying DC level having a value proportional to either approximate true viscosity of the fluid 14 or to the fluid shearing torque applied to the spindle 13, depending upon the setting of the mode selector switch S2. For some purposes it is desirable to directly display the signals, while for other purposes relatively long term averaging thereof may be desired.

Such long term averaging is provided by the boxcar averager 69, or by any other suitable analog or digital averaging circuit. The averager 69 does not form any part of the present invention, and therefore is not described in further detail.

A digital multimeter 70 is coupled through a selector switch S4, to read either the signal on line 68, the relatively long term averaged signal from the averager 69 on line 71, or the peak fluid torque or yield point signal on line 82 (as hereafter described).

Similarly, a selector switch S5 selects either the signal on line 68 or the averaged signal on line 71, for coupling to the Y or vertical deflection input terminal 72 of plotter 41 via plotter drive amplifier A6 and associated input and feedback resistors 73 and 74 respectively.

In order to provide a measurement of fluid yield point, a peak fluid torque detection and storage circuit is provided, comprising switches S6 and S7, operational amplifiers A10 and A11, and associated circuitry.

It is frequently necessary to determine the torque required to overcome the inertial or "static" friction of a viscous mass. The rotary viscometer herein described is capable of such measurement, in that it determines viscous torque by monitoring the motor current required to drive a motor having a linear current-to-torque characteristic to turn a rotary spindle and cup system. When used to make such peak viscous torque measurements, by starting the motor with the spindle immersed in the fluid, the spindle should have suitably small dimensions so that the motor/servo system will not overload as the spindle starts to turn in the liquid. For high yield point fluids, spindle dimensions may have to be much smaller when the apparatus is used in this peak measurement mode, than when it is employed for conventional torque plots and for true viscosity plots.

The amplifier A10 is connected to function as a voltage following amplifier for impedance isolation purposes. The amplifier gain is determined by input and feedback resistors 83 and 84 respectively. The input of the amplifier A10 is connected to the output of normalizing amplifier A3 through a limiter comprising the series combination of resistor 85 and parallel back-to-back diodes 86 and 87, which serve to prevent latching of the peak detection circuit.

The output of amplifier A10 is connected to peak detection and storage amplifier A11 through the series combination of input resistor 88 and diode 89, with a capacitor 90 being connected between the output and input terminals of amplifer A11 to provide peak detection and storage of the viscous torque signal. A shorting switch S7 serves to reset the circuit by discharging the capacitor 90 after each peak measurement has been made. The output of amplifier A11 is fed back to the input of amplifier A10 via resistor 91 to provide operation independent of the diode loss across diode 89. The switch S6 disconnects the capacitor 50 from the feedback circuit of normalizing amplifier A3 in the peak detection mode, because said capacitor is large and introduces an undesirable propagation delay. The amplifier A11 is preferably a low offset type suitable for use with sample-and-hold type circuitry. The memory capacitor 90 should have low leakage; however, because the required storage time is usually relatively short, a Mylar (a type of polyester) or polycarbonate capacitor is adequate for this purpose.

If desired, rather than varying the rotational speed of the shaft 17 during each step of the output of the staircase generator 28, the circuitry can be somewhat simplified (with a corresponding reduction in performance) by taking one sample of each step, and adjusting the step height to correspond to the desired difference between successive samples [rather than using the torque differential offset system previously described]. Such a change would involve elimination of switch section S2a and summing resistor 31, and a reduction in complexity of the switching of the counter 24. With these changes relay K1 would be energized for sampling during every second stage of the staircase waveform on line 29, while relay K2 would be energized on alternate steps. Thus the higher torque value of each set is sampled on odd numbered steps and the lowers torque value thereof is sampled on even numbered steps. In such an event, to avoid having every second step negative, there may be provided a phase change or an absolute detector coupled to the output of amplifier A5.

With the aforementioned change, however, there would be a marked deterioration in performance, since if the same speed difference between readings of each set were maintained (i.e. 0.4, 4 or 40 rpm), the number of samples taken during each sweep of the entire range would be reduced from 225 to 11. Alternatively, if the nesting of successive steps were eliminated but the small step increment were retained, with the same 255 steps per measurement cycle, a high noise level would result due to the measurement of small differences between relatively large values.

Preferably, for low viscosity measurements, the weight of the spindle 13, the shaft 17 and associated suspended mass, should be such that the spindle 13 "almost floats" in the fluid 14, or preferably is at least partially supported by the buoyancy effect of the displaced portion of the fluid 14, so as to minimize thrust forces (and consequent friction losses and resulting noise) on the bearings of the motor 16.

While the system has been described on the basis that during each step of the staircase waveform the torque reading corresponding to the higher speed is taken before the torque reading corresponding to the lower speed, the circuit operation may of course be altered to reverse this order of measurement, for example by inverting the signal applied to summing resistor 31 between the output of delay circuit 25 and input to switch section S2a.

The Couette system, where the cup rotates around a stationary inner cylinder, can substitute for the coaxial cylinder system described above. The viscometer can be used, e.g., with conical, cone and plate as well as spherical and disc type rotors (spindles). Discs commercially available for use with spring type rotary viscometers are readily adapted for use in the incremental rotary viscometer of the present invention. Moreover, the automatic speed sweep, direct digital readout and X-Y plotting features of the present invention can be advantageously utilized with such commercially available discs. The viscometer spindle may be inserted into large containers of fluid and when suitably calibrated can generate highly reproducible and accurate viscosity measurements in such "infinite" media. The viscometer may be satisfactorily operated at speeds over 1,000 rpm in order to measure viscosity at high shear rates.

We claim:
1. A process for determining the viscosity of or viscous loss in a fluid, comprising the steps of:
   (a) providing a rotatable fluid shearing spindle adapted for immersion in said fluid;
   (b) rotating said spindle at a first speed determined by a speed sweep signal, said first speed lying within a predetermined speed range having upper and lower speed limits;
   (c) measuring the torque exerted by said fluid on said spindle at said first speed;
   (d) subsequently varying said first speed by a given speed difference, to a second speed within said range, said first and second speeds comprising a set of speed values;
   (e) measuring the torque exerted by said fluid on said spindle at said second speed;

(f) providing a viscosity or viscous loss indicating signal for said set corresponding to the difference between said first and second speed torque values; and (g) thereafter causing said spindle speed to successively assume other sets of first and second speed values throughout said range, in accordance with said speed sweep signal, and repeating steps (c) through (f) for each of said successive other sets of speed values.

2. The process according to claim 1, wherein said speed sweep signal has a staircase type of waveform, each step having a first portion of amplitude corresponding to said first value of the corresponding set of speed values, and a second portion of amplitude corresponding to said second value of the corresponding set of speed values.

3. The process according to claim 2, wherein the amplitude difference between said first and second portions of each step corresponding to the speed difference between the first and second speed values of each set is substantially greater than the amplitude difference between corresponding portions of adjacent steps.

4. The process according to claim 1, wherein said given speed difference between said first and second speeds is the same for all speed sets within said range.

5. The process according to claim 1, wherein said spindle speed is caused to sequentially assume sets of first and second speed values, the speed increment between each first speed value and the first speed value of the preceding set being equal to the speed increment between each second speed value and the second speed value of the preceding set.

6. The process according to claim 4, wherein said spindle speed is caused to sequentially assume sets of first and second speed values, the speed increment between each first speed value and the first speed value of the preceding set being equal to the speed increment between each second speed value and the second speed value of the preceding set.

7. The process according to claim 5 or 6, wherein said speed increment has a value substantially less than said speed difference.

8. The process according to claim 1, wherein said spindle is rotated after immersion thereof in said fluid.

9. Apparatus for determining the viscosity of or viscous loss in a fluid, comprising:
(a) a rotatable fluid shearing spindle adapted for immersion in said fluid;
(b) a motor and associated means for rotating said spindle at a first speed determined by a speed sweep signal, said first speed lying within a predetermined speed range having upper and lower speed limits, and for providing an output signal indicative of the torque applied to said spindle by said fluid;
(c) a first sample-and-hold circuit for storing the value of said output signal indicative of the torque exerted by said fluid on said spindle at said first speed;
(d) means for subsequently varying said first speed by a given speed difference, to a second speed within said range, said first and second speeds comprising a set of speed values;
(e) a second sample-and-hold circuit for storing the value of said output signal indicative of the torque exerted by said fluid on said spindle at said second speed;

(f) a difference circuit means for providing a viscosity or viscous loss indicating signal corresponding to the difference between said first and second speed torque values; and (g) means for varying said sweep speed signal to thereafter cause said first and second spindle speeds to successively assume other sets of speed values throughout said range.

10. The apparatus according to claim 9, wherein the speed difference between said first and second values is the same for all of said sets.

11. The apparatus according to claim 9, wherein said speed sweep signal has a staircase type of waveform, each step having a first portion of amplitude corresponding to said first value of the corresponding set of speed values, and a second portion of amplitude corresponding to said second value of the corresponding set of speed values, further comprising means for synchronizing the first and second portions of each step of said speed sweep signal with the sampling periods of said first and second sample-and-hold circuits respectively.

12. The apparatus according to claim 10, wherein said speed sweep signal has a staircase type of waveform, each step having a first portion of amplitude corresponding to said first value of the corresponding set of speed values, and a second portion of amplitude corresponding to said second value of the corresponding set of speed values, further comprising means for synchronizing the first and second portions of each step of said speed sweep signal with the sampling periods of said first and second sample-and-hold circuits respectively.

13. The apparatus according to claim 10, 11 or 12, wherein the amplitude difference between said first and second portions of each step corresponding to the speed difference between the first and second speed values of each set is substantially greater than the amplitude difference between corresponding portions of adjacent steps.

14. The apparatus according to claim 9, 10, 11 or 12 wherein said given speed difference between said first and second speeds is the same for all speed sets within said range.

15. The apparatus according to claim 9, 10, 11 or 12, further comprising means for causing said spindle speed to sequentially assume sets of first and second speed values, the speed increment between each first speed value and the first speed value of the preceding set being equal to the speed increment between each second speed value and the second speed value of the preceding set.

16. The apparatus according to claim 15, wherein said speed increment has a value substantially less than said speed difference.

17. The apparatus according to claim 11 or 12, wherein each step of said speed sweep signal is synchronized with the rotation of said spindle.

18. The apparatus according to claim 9, further comprising means for filtering said output signal before the same is coupled to each of said sample-and-hold means.

19. The apparatus according to claim 9, further comprising means for plotting a graph of said viscosity or viscous loss indicating signal as a function of spindle speed.

20. The apparatus according to claim 9, further comprising manually operable means for selecting a desired measurement speed and providing a readout of viscous torque and fluid viscosity at said selected speed.

21. The apparatus according to claim 9, further comprising means for determining and storing the peak value of said output signal indicative of the torque applied by said spindle to said fluid, said peak value being representative of the yield point of said fluid.

22. Apparatus for generating a signal, in a series of speed measurement cycles, approximating the true viscosity of a Newtonian or non-Newtonian fluid at shear rates corresponding to a range of spindle rotation speeds extending between predetermined upper and lower speed limits, comprising:

(a) a rotatable fluid shearing spindle mounted on a shaft and adapted for immersion in said fluid;
(b) an electric motor for rotating said shaft, the current through a drive winding of said motor being proportional to the torque developed thereby;
(c) a tachometer coupled to said shaft;
(d) a pulse generator coupled to said shaft for generating timing pulses in synchronization with the rotation of the shaft;
(e) first counting means coupled to said pulse generator for counting said timing pulses;
(f) first circuit means coupled to said first counting means for defining the duration of each of said speed measurement cycles;
(g) first switching means coupled to said first counting means for repetitive actuation during selected first portions of each of said speed measurement cycles;
(h) second switching means coupled to said first counting means for repetitive actuation during selected second portions of each of said speed measurement cycles;
(i) staircase generating means including second counting means synchronously coupled to said first counting means and said first circuit means for generating a staircase waveform each step of which has a duration corresponding to the duration of one of said speed measurement cycles;
(j) summing amplifier means having input terminals coupled to said tachometer, said first circuit means and said staircase generating means and an output terminal coupled to said motor drive winding for varying the rotational speed of said shaft in stepwise fashion between said upper and lower speed limits of said range, each speed step having (A) a duration equal to one measurement cycle, (B) a first part corresponding to said first portion of said speed measurement cycle, and (C) a second part corresponding to said second portion of said speed measurement cycle, the amplitude difference between the first and second parts of each step having a constant value defining a desired speed difference, the amplitude difference between the first part of each step and the first part of the preceding step being equal to the amplitude difference between the second part of each step and the second part of the preceding step and having a constant value defining a desired speed increment;
(k) second circuit means responsive to the current through said motor drive winding for providing a torque indicating signal;
(l) first sample-and-hold means coupled to said first switching means and said second circuit means for sampling said torque indicating signal at times corresponding to the first parts of each of said speed steps;
(m) second sample-and-hold means coupled to said second switching means and said second circuit means for sampling said torque indicating signal at times corresponding to the second parts of each of said speed steps;
(n) difference circuit means coupled to said first and second sample-and-hold means for providing a true viscosity approximating signal corresponding to the difference between the outputs of said first and second sample-and-hold means; and
(o) means for displaying said true viscosity approximating signal.

23. The apparatus according to claim 22, wherein said difference circuit means includes means for sampling the output of said second sample-and-hold means at times corresponding to the first parts of each of said speed steps.

24. The apparatus according to claim 22 or 23, wherein the duration of each of said speed steps corresponds to a predetermined number of revolutions of said shaft.

25. The apparatus according to claim 22, wherein said displaying means comprises an X-Y coordinate plotter having an X axis input coupled to said staircase generating means and a Y axis input for receiving said true viscosity approximating signal.

* * * * *

UNITED STATES PATENT AND TRADEMARK OFFICE
CERTIFICATE OF CORRECTION

PATENT NO. : 4,299,119
DATED : November 10, 1981
INVENTOR(S) : J. Vincent Fitzgerald et al.

It is certified that error appears in the above—identified patent and that said Letters Patent is hereby corrected as shown below:

On The Title Page, the assignee should read

-- National Metal and Refining Company, Inc. --.

Signed and Sealed this

Second Day of March 1982

[SEAL]

*Attest:*

GERALD J. MOSSINGHOFF

*Attesting Officer*     *Commissioner of Patents and Trademarks*